(12) United States Patent
Peterson et al.

(10) Patent No.: US 10,016,608 B2
(45) Date of Patent: *Jul. 10, 2018

(54) SYSTEM AND METHOD FOR INTRODUCING TISSUE STIMULATION LEAD INTO PATIENT USING REAL-TIME COUPLING EFFICIENCY MEASUREMENTS

(71) Applicant: Boston Scientific Neuromodulation Corporation, Valencia, CA (US)

(72) Inventors: David K. L. Peterson, Valencia, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/264,337

(22) Filed: Sep. 13, 2016

(65) Prior Publication Data

US 2017/0001023 A1    Jan. 5, 2017

Related U.S. Application Data

(63) Continuation of application No. 13/244,458, filed on Sep. 24, 2011, now Pat. No. 9,446,249.

(Continued)

(51) Int. Cl.
*A61N 1/36* (2006.01)
*A61N 1/372* (2006.01)
*A61N 1/05* (2006.01)

(52) U.S. Cl.
CPC ....... *A61N 1/37247* (2013.01); *A61N 1/0551* (2013.01); *A61N 1/3605* (2013.01); *A61N 1/36185* (2013.01); *A61N 1/372* (2013.01)

(58) Field of Classification Search
CPC .......................... A61N 1/36185; A61N 1/372
See application file for complete search history.

(56) References Cited

U.S. PATENT DOCUMENTS

| 6,516,227 B1 | 2/2003 | Meadows et al. |
| 6,993,384 B2 | 1/2006 | Bradley et al. |
| (Continued) | | |

FOREIGN PATENT DOCUMENTS

| EP | 1510182 A2 | 3/2005 |
| EP | 2629845 B1 | 9/2016 |
| (Continued) | | |

OTHER PUBLICATIONS

"U.S. Appl. No. 13/244,458, Non Final Office Action dated Mar. 3, 2015", 13 pgs.

(Continued)

*Primary Examiner* — Amanda Patton
(74) *Attorney, Agent, or Firm* — Schwegman Lundberg & Woessner, P.A.

(57) ABSTRACT

A system and method for locating an implantable tissue stimulation lead within a patient. A measurement indicative of a coupling efficiency between the tissue stimulation lead and tissue at a location is taken. The location of the tissue stimulation lead relative to the tissue is tracked. Coupling efficiency information based on the measurement from the monitoring device is generated, tracking information based on the tissue stimulation lead location is generated, and the coupling efficiency information and tracking information is concurrently conveyed to the user.

20 Claims, 14 Drawing Sheets

Related U.S. Application Data

(60) Provisional application No. 61/405,535, filed on Oct. 21, 2010.

(56) References Cited

U.S. PATENT DOCUMENTS

| | | | |
|---|---|---|---|
| 7,239,920 | B1 | 7/2007 | Thacker et al. |
| 7,317,948 | B1 | 1/2008 | King et al. |
| 8,010,208 | B2 | 8/2011 | Nimer et al. |
| 9,446,249 | B2* | 9/2016 | Peterson ............ A61N 1/36185 |
| 2003/0139781 | A1 | 7/2003 | Bradley et al. |
| 2006/0155333 | A1* | 7/2006 | Goetz ...................... A61N 1/08 607/2 |
| 2006/0224222 | A1 | 10/2006 | Bradley |
| 2007/0203546 | A1 | 8/2007 | Stone et al. |
| 2008/0081982 | A1 | 4/2008 | Simon et al. |
| 2008/0146928 | A1 | 6/2008 | Dala-krishna |
| 2009/0157155 | A1* | 6/2009 | Bradley ............. A61N 1/37247 607/116 |
| 2010/0100153 | A1 | 4/2010 | Carlson et al. |
| 2010/0152801 | A1 | 6/2010 | Koh et al. |
| 2012/0101537 | A1 | 4/2012 | Peterson et al. |

FOREIGN PATENT DOCUMENTS

| | | |
|---|---|---|
| JP | 2006035226 A | 2/2006 |
| JP | 2008534168 A | 8/2008 |
| JP | 2008539857 A | 11/2008 |
| WO | WO-2006117773 A1 | 11/2006 |
| WO | WO2012054183 | 4/2012 |

OTHER PUBLICATIONS

"U.S. Appl. No. 13/244,458, Non Final Office Action dated Aug. 5, 2014", 8 pgs.
"U.S. Appl. No. 13/244,458, Non Final Office Action dated Sep. 10, 2015", 13 pgs.
"U.S. Appl. No. 13/244,458, Non Final Office Action dated Nov. 3, 2014", 9 pgs.
"U.S. Appl. No. 13/244,458, Notice of Allowance dated May 20, 2016", 5 pgs.
"U.S. Appl. No. 13/244,458, Response filed Jan. 7, 2016 to Non Final Office Action dated Sep. 10, 2015", 9 pgs.
"U.S. Appl. No. 13/244,458, Response filed Feb. 3, 2015 to Non Final Office Action dated Nov. 3, 2014", 10 pgs.
"U.S. Appl. No. 13/244,458, Response filed Jun. 3, 2015 to Non Final Office Action dated Mar. 3, 2015", 10 pgs.
"U.S. Appl. No. 13/244,458, Response filed Jul. 8, 2014 to Restriction Requirement dated May 28, 2014", 1 pg.
"U.S. Appl. No. 13/244,458, Response filed Sep. 24, 2014 to Non Final Office Action dated Aug. 5, 2014", 6 pgs.
"U.S. Appl. No. 13/244,458, Restriction Requirement dated May 28, 2014", 5 pgs.
"Australian Application Serial No. 2011318500, First Examiner Report dated Jun. 19, 2015", 3 pgs.
"Australian Application Serial No. 2011318500, Subsequent Examiners Report dated Dec. 16, 2015", 3 pgs.
"European Application Serial No. 11769985.0, Examination Notification Art. 94(3) dated Jun. 27, 2014", 4 pgs.
"European Application Serial No. 11769985.0, Response filed Nov. 7, 2014 to Examination Notification Art. 94(3) dated Jun. 27, 2014", 9 pgs.
"International Application Serial No. PCT/US2011/053182, International Preliminary Report on Patentability dated May 2, 2013", 9 pgs.
"International Application Serial No. PCT/US2011/053182, International Search Report dated Dec. 27, 2011", 4 pgs.
"International Application Serial No. PCT/US2011/053182, Written Opinion dated Dec. 27, 2011", 7 pgs.
"Japanese Application Serial No. 2013-534922, Amendment filed Jun. 21, 2013", 3 pgs.
"Japanese Application Serial No. 2013-534922, Office Action dated Apr. 30, 2015", With English Translation, 5 pgs.
"Canadian Application Serial No. 2,815,313, Office Action dated Jun. 14, 2017", 3 pgs.
"Japanese Application Serial No. 2013-534922, Examiners Decision of Final Refusal dated Jan. 18, 2016", (English Translation), 5 pgs.

* cited by examiner

SYSTEM AND METHOD FOR INTRODUCING TISSUE STIMULATION LEAD INTO PATIENT USING REAL-TIME COUPLING EFFICIENCY MEASUREMENTS

RELATED APPLICATION DATA

The present application is a continuation of U.S. application Ser. No. 13/244,458, filed Sep. 24, 2011, which claims the benefit under 35 U.S.C. § 119 to U.S. provisional patent application Ser. No. 61/405,535, filed Oct. 21, 2010. The foregoing applications are hereby incorporated by reference into the present application in their entirety.

FIELD OF THE INVENTION

The present invention relates to tissue stimulation systems, and more particularly, to apparatus and methods for introducing tissue stimulation leads into patients.

BACKGROUND OF THE INVENTION

Implantable tissue stimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

These implantable tissue stimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the tissue stimulation lead(s) or indirectly to the tissue stimulation lead(s) via a lead extension. Thus, electrical pulses can be delivered from the neurostimulator to the tissue stimulation leads to stimulate the tissue and provide the desired efficacious therapy to the patient. The tissue stimulation system may further comprise a handheld patient programmer in the form of a remote control (RC) to remotely instruct the neurostimulator to generate electrical stimulation pulses in accordance with selected stimulation parameters. A typical stimulation parameter set may include the electrodes that are acting as anodes or cathodes, as well as the amplitude, duration, and rate of the stimulation pulses. The RC may, itself, be programmed by a clinician, for example, by using a clinician's programmer (CP), which typically includes a general purpose computer, such as a laptop, with a programming software package installed thereon. Typically, the RC can only control the neurostimulator in a limited manner (e.g., by only selecting a program or adjusting the pulse amplitude or pulse width), whereas the CP can be used to control all of the stimulation parameters, including which electrodes are cathodes or anodes.

In the context of an SCS procedure, one or more stimulation leads are introduced through the patient's back into the epidural space, such that the electrodes carried by the leads are arranged in a desired pattern and spacing to create an electrode array. One type of commercially available stimulation leads is a percutaneous lead, which comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two or more percutaneous leads are placed down the respective sides of the midline of the spinal cord, and if a third lead is used, down the midline of the spinal cord. After proper placement of the tissue stimulation leads at the target area of the spinal cord, the leads are anchored in place at an exit site to prevent movement of the tissue stimulation leads. To facilitate the location of the neurostimulator away from the exit point of the tissue stimulation leads, lead extensions are sometimes used.

The tissue stimulation leads, or the lead extensions, are then connected to the IPG, which can then be operated to generate electrical pulses that are delivered, through the electrodes, to the targeted tissue, and in particular, the dorsal column and dorsal root fibers within the spinal cord. The stimulation creates the sensation known as paresthesia, which can be characterized as an alternative sensation that replaces the pain signals sensed by the patient. Intra-operatively (i.e., during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computer program, such as Bionic Navigator®, available from Boston Scientific Neuromodulation Corporation, can be incorporated in a clinician's programmer (CP) (briefly discussed above) to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the tissue stimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy, and as such, precise positioning of the leads proximal to the targets of stimulation is critical to the success of the therapy.

One important parameter that can influence the electrical field generated by stimulation electrodes, and thus the proper placement of the leads, is the electrical conductivity environment due to the tissue characteristics surrounding the electrodes. This is often a secondary concern to the clinician, who will typically place the tissue stimulation leads based on anatomic (fluoroscopy, ultrasound, etc.) and physiologic (compound action potentials, EMG, etc.) landmarks, and then anticipate that the electrical environment seen by the electrodes will promote good coupling efficiency between the tissue stimulation leads and the target tissue, and will therefore not significantly affect the stimulation therapy.

However, it cannot always be assumed that the coupling efficiency is at a level high enough to achieve optimum performance even when the position of the tissue stimulation leads relative to the tissue appears to promote good coupling efficiency under conventional imaging. For example, in the case of SCS, when the tissue stimulation leads are viewed in the epidural space of the patient under a conventional anterior fluoroscopic image, the leads may appear properly located relative to the spinal cord. In reality, however, portions of the tissue stimulation leads may be dorsally located from the spinal cord a relatively far distance, which will not be appreciated from a conventional anterior fluoroscopic image. As a result, the coupling efficiency between the electrodes of the tissue stimulation leads that are relatively far from the spinal cord may be quite low, which may adversely affect the performance of the tissue stimulation system.

For example, in single-source tissue stimulation systems, the impedance seen at each electrode may influence the amount of electrical current that can be delivered from each electrode, and thereby shape the electrical field in a non-controllable manner. If the impedance is high enough, coupling efficiency between the electrodes and the target tissue to be stimulated will be so low that stimulation performance will be significantly degraded. Even for multi-source tissue stimulation systems that precisely control the magnitude of electrical current at each electrode, the occurrence of a low coupling efficiency between the electrodes and the surrounding tissue due to high electrode impedance, forces the system to use more energy that what would otherwise be necessary to maintain stimulation performance. As a result, an excessive amount of compliance voltage may need to be generated in order to effectively supply stimulation energy to the electrodes if the tissue stimulation system uses current-controlled sources, thereby resulting in an inefficient use of the battery power, or the stimulation energy supplied to the electrode may be otherwise inadequate if the tissue stimulation system uses voltage-controlled sources.

There, thus, remains a need for a system and method for positioning tissue stimulation leads within a tissue region of the patient that provides a suitable electrical conductivity environment for optimizing the conveyance of electrical stimulation energy from the tissue stimulation leads.

SUMMARY OF THE INVENTION

In accordance with a first aspect of the present inventions, a system for locating an implantable tissue stimulation lead within a patient is provided.

The system comprises a monitoring device configured for taking a measurement indicative of a coupling efficiency between the tissue stimulation lead and tissue at a location. In one embodiment, the monitoring device is configured for taking the measurement by conveying an electrical signal between the tissue stimulation lead and the tissue, and measuring an electrical parameter (e.g., an impedance or field potential) in response to the conveyance of the electrical signal. In an optional embodiment, the monitoring device is a neurostimulator further configured for delivering stimulation energy to the implantable tissue stimulation lead.

The system further comprises a tracking system configured for tracking the location of the tissue stimulation lead relative to the tissue, and an external control device configured for generating coupling efficiency information based on the measurement from the monitoring device, for generating tracking information based on the tissue stimulation lead location, and concurrently displaying the coupling efficiency information (e.g., as one or more numerical values or one or more graphs) and tracking information to the user.

In one embodiment, the tissue stimulation lead is configured for being introduced within the patient at different locations along a trajectory path. In this case, the monitoring device may be configured for taking measurements indicating the coupling efficiencies between the tissue stimulation lead and the tissue at the different locations, the tracking system may be configured for tracking the different locations of the tissue stimulation lead, and the external control device may be configured for generating the coupling efficiency information based on the measurements from the monitoring device, and for generating the tracking information based on the tissue stimulation lead locations. The displayed tracking information may concurrently indicate the different locations of the tissue stimulation lead relative to the tissue. The tracking information may be indicative of the different locations of the tissue stimulation lead relative to an anatomical structure of the patient.

In accordance with a second aspect of the present inventions, an external control device for use with an implantable tissue stimulation lead, a monitoring device configured for taking a measurement indicative of coupling efficiency between the tissue stimulation lead and tissue, and a tracking system configured for tracking a location of the tissue stimulation lead relative to the tissue, is provided.

The external control device comprises input circuitry configured for obtaining the measurement from the monitoring device and the tissue stimulation lead location from the tracking system. The external control device further comprises processing circuitry configured for generating coupling efficiency information based on the measurement received by the input circuitry, for generating tracking information based on the tissue stimulation lead location received by the input circuitry, and for integrating the coupling efficiency information and tracking information together. The external control device further comprises a user interface configured for displaying the integrated coupling efficiency information (e.g., as one or more numerical values or one or more graphs) and tracking information.

In accordance with a third aspect of the present inventions, a method of implanting a tissue stimulation lead within tissue of a patient is provided.

The method comprises advancing the tissue stimulation lead within the patient at different locations along a trajectory path (e.g., within an epidural space of the patient), and generating coupling efficiency information indicative of coupling efficiencies between the tissue stimulation lead and the tissue when the tissue stimulation lead is respectively at the different locations. One method the coupling efficiency information is generated by conveying electrical signals between the tissue stimulation lead and tissue of the patient when the tissue stimulation lead is at the different locations, and measuring electrical parameters (e.g., an impedance or a field potential) in response to the conveyance of the electrical signals.

The method further comprises conveying the coupling efficiency information to a user (e.g., by displaying the coupling efficiency information), and affixing the tissue stimulation lead at a suitable one of the different locations based on the coupling efficiency information conveyed to the user. In one method, the suitable location is the location at which the coupling efficiency information indicates the coupling efficiency between the tissue stimulation lead and the tissue as being the highest.

The tissue stimulation lead may carry a plurality of electrodes, in which case, the method may comprise determining raw coupling efficiency data between the electrodes and the tissue when the tissue stimulation lead is at each of the different locations, and the coupling efficiency information between the tissue stimulation lead and the tissue may be derived from the determined raw coupling efficiency data. After the tissue stimulation lead is placed at each location, the measurements and processing are preferably performed in real-time. That is, the time elapsed between the placement of the tissue stimulation lead at each of the different locations along the trajectory path and the conveyance of the coupling efficiency information at each respective location is less than one second.

Another method further comprises generating tracking information indicative of the different locations of the tissue stimulation lead, and displaying the tracking information with the coupling efficiency information. The coupling efficiency information may be, e.g., one or more numerical values or one or more graphs. In this case, the displayed tracking information may optionally concurrently indicate the different locations of the tissue stimulation lead. The tracking information may be indicative of the different locations of the tissue stimulation lead relative to an anatomical structure of the patient.

An optional method further comprises conveying stimulation energy from the tissue stimulation lead into the tissue at the different locations along the trajectory path, and performing a corrective action (e.g., repositioning the tissue stimulation lead or adjusting at least one stimulation parameter of the conveyed stimulation energy) if the coupling efficiency information conveyed to the user indicates the coupling efficiency between the tissue stimulation lead and the tissue as being low at one of the different locations.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
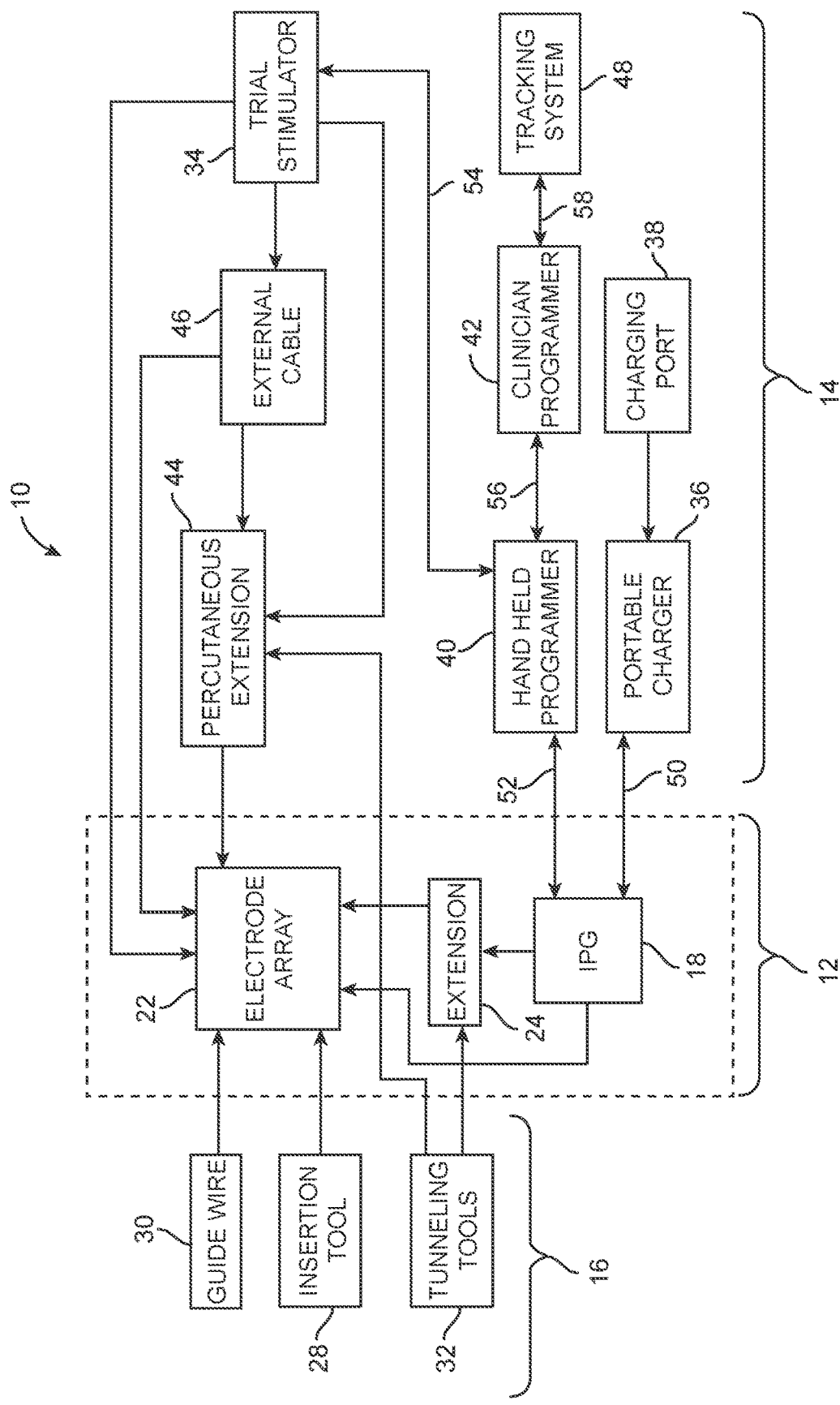
FIG. 1 is block diagram of a spinal cord stimulation (SCS) system arranged in accordance with the present inventions.
Figure 2:
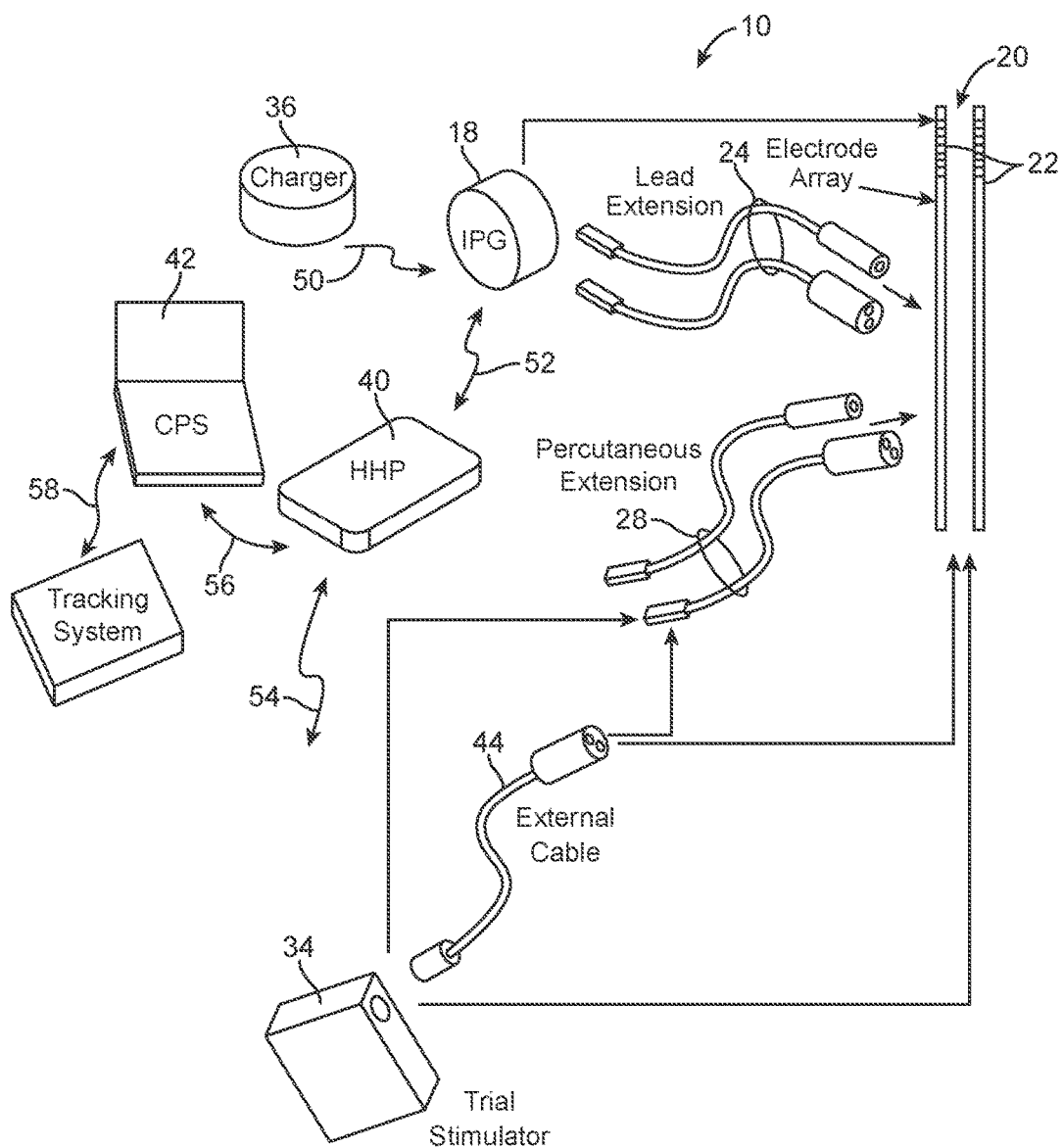
FIG. 2 is a perspective view of the SCS system of FIG. 1.
Figure 3:
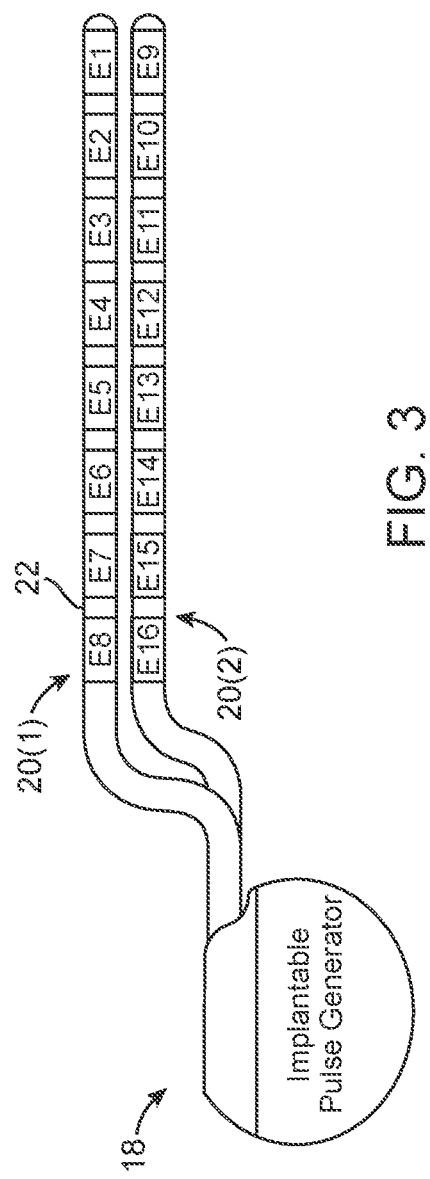
FIG. 3 is a plan view of an implantable pulse generator (IPG) and two percutaneous tissue stimulation leads used in the SCS system of FIG. 1.

Turning first to FIGS. 1-3, an exemplary SCS system 10 arranged in accordance with one embodiment of the present inventions will be described. The system 10 comprises components that may be subdivided into three broad categories: (1) implantable components 12; (2) external components 14; and (3) surgical components 16. The implantable components 12 include an implantable neurostimulator in the form of an implantable pulse generator (IPG) 18, one or more tissue stimulation leads 20 carrying an array of electrodes 22 (shown in FIG. 2), and a lead extension 24 (as needed).

In the illustrated embodiment, the tissue stimulation leads 20 are percutaneous leads, and to this end, the electrodes 22 are arranged in-line along the tissue stimulation leads 20. Alternatively, the tissue stimulation leads 20 may be replaced with a single paddle stimulation lead. In the illustrated embodiment shown in FIG. 3, the first stimulation lead 20(1) has eight electrodes 22 (labeled E1-E8), and the second stimulation lead 20(2) includes eight electrodes 22 (labeled E9-E16). The actual number of leads and electrodes will, of course, vary according to the intended application.

The IPG 18 can provide electrical stimulation through at least some of the sixteen electrodes E1 through E16 included within the electrode array 22. To this end, the IPG 18 may be connected directly to the tissue stimulation leads 20, or indirectly to stimulation leads 20 via the lead extension 24. The IPG 18 includes stimulating electrical circuitry, processing circuitry, a power source (e.g., a rechargeable battery) or receiver, and telemetry circuitry, all contained within a hermetically sealed, biocompatible, case.

Figure 4:
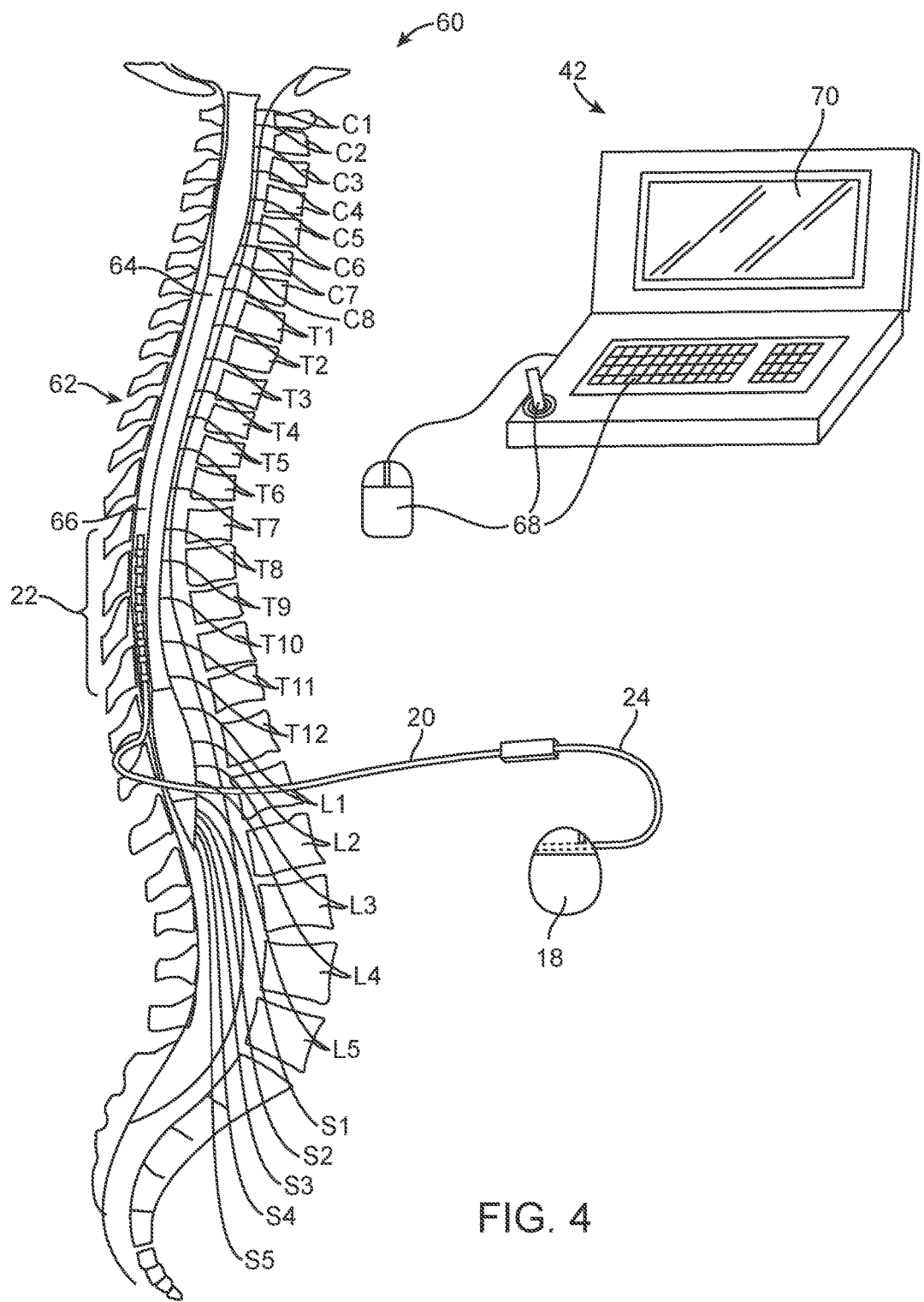
FIG. 4 is a plan view of the SCS system of FIG. 1 in use with a patient.
Figure 5A:
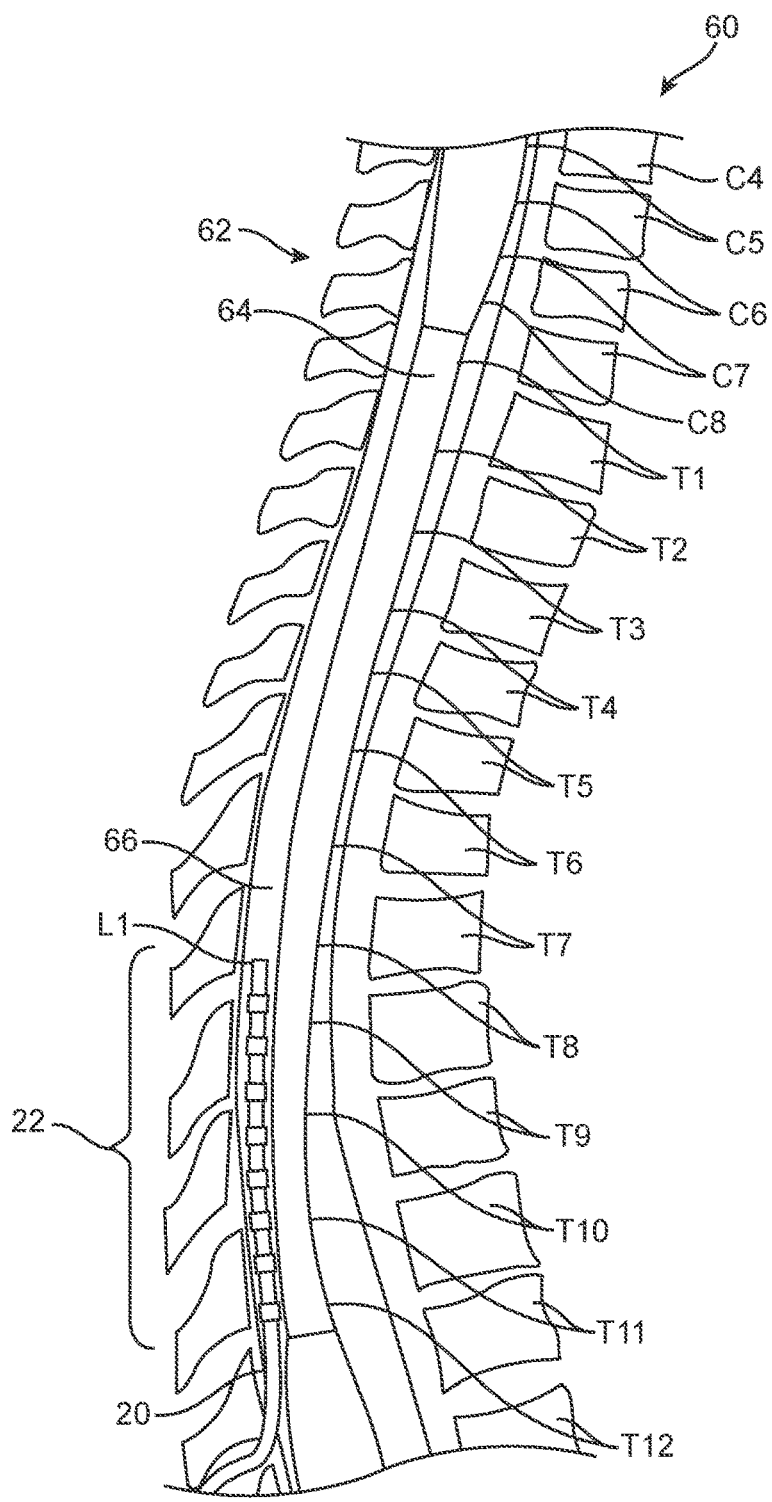
FIGS. 5A-5C are plan views of a tissue stimulation lead being introduced within the epidural space of the patient at three different locations.
Figure 5B:
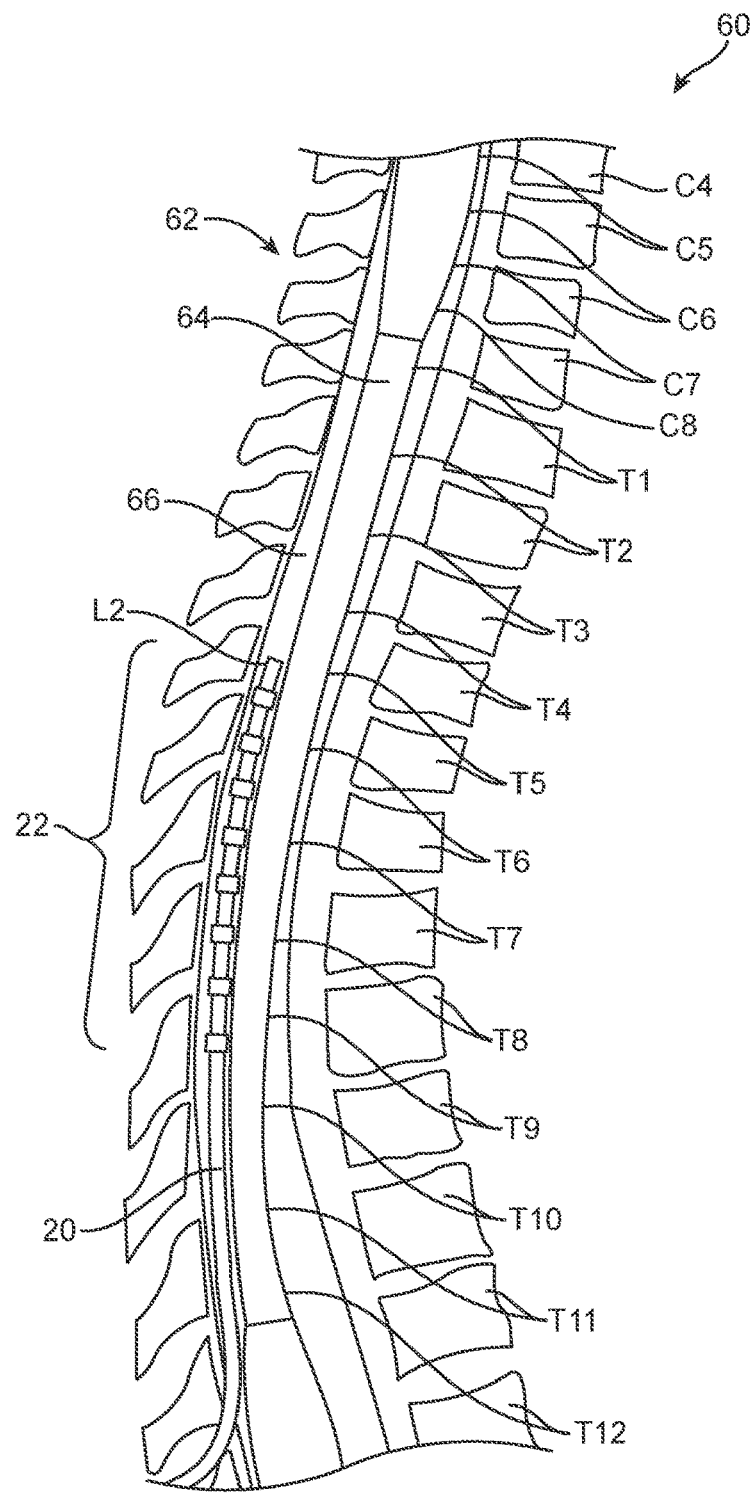
Figure 5C:
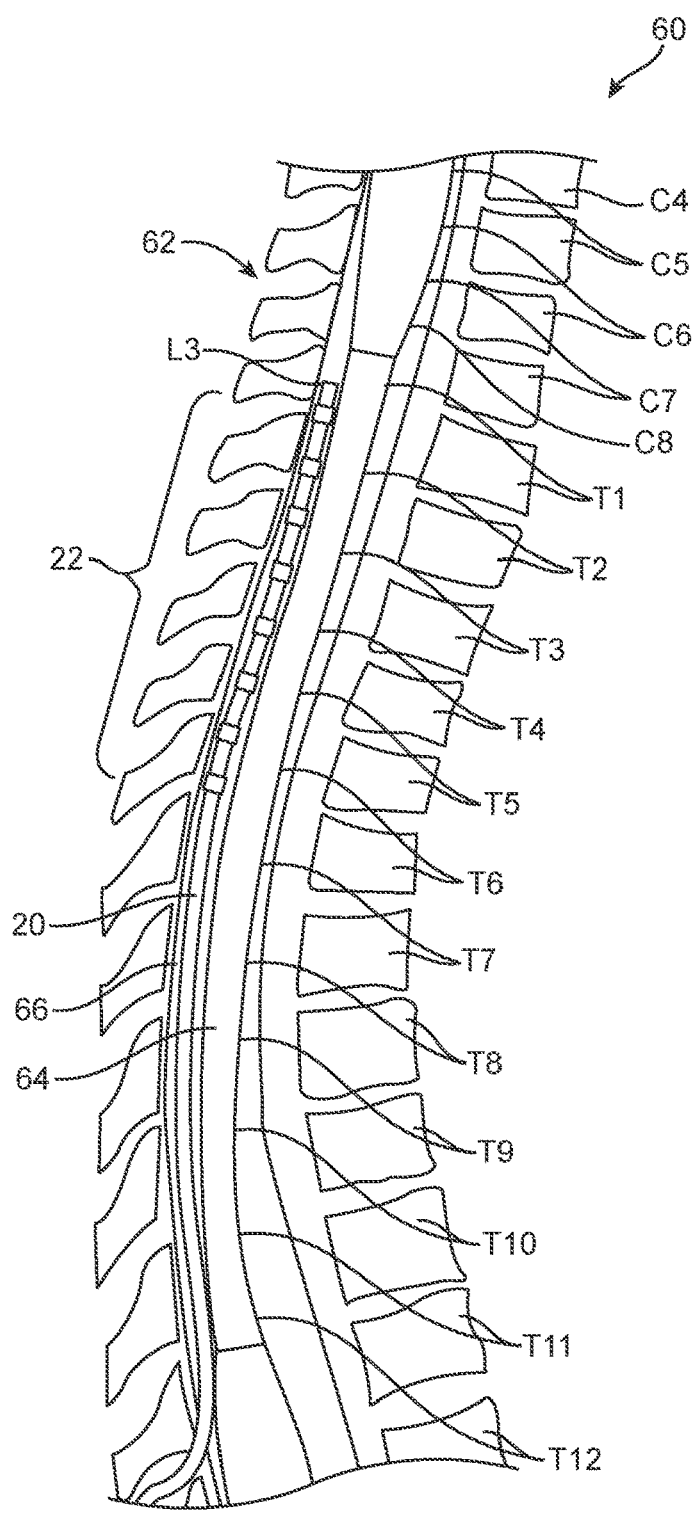

As shown in FIG. 4, the implantable components 12, which includes the IPG 18, the tissue stimulation lead(s) 20, and if needed, the lead extension(s) 24 may be implanted within a patient 60 using the surgical components 16, which include an insertion tool, such as a hollow needle 28, a guidewire or stylet 30, and tunneling tools 32 (shown in FIG. 1). The tissue stimulation lead(s) 20 may be percutaneously implanted within the spinal column 62 of the patient 60 through the use of the needle 28 and the stylet 30. The preferred placement of the tissue stimulation leads 20 is such that the electrode array 22 is adjacent (i.e., resting upon) the dura nearest the target area of the spinal cord 64 to be stimulated. For example, the needle 28 with stylet 30 is inserted through the back into the epidural space 66 of the patient 60. The stylet 30 is then removed from the needle 28 to create a hollow opening, and a syringe (not shown) is inserted in the needle 28 to inject saline (3-5 cc) to ensure the needle tip has entered the epidural space 66. One of the tissue stimulation leads 20 is then passed through the needle 28 into the epidural space 66. The other stimulation lead 20 is introduced into the epidural space 66 in the same manner. After the tissue stimulation leads 20 are placed, the needle 28 is then pulled out, and an anchor (not shown) is placed around the tissue stimulation leads 20 at the exit site and sutured in place to prevent movement of the tissue stimulation leads 20.

Due to the lack of space near the location where the tissue stimulation leads 20 exit the spinal column 62, the selected IPG 18 is generally implanted in a surgically-made pocket either in the abdomen or above the buttocks. The IPG 18 may, of course, also be implanted in other locations of the patient's body. The lead extension(s) 24 facilitate locating the IPG 18 away from the exit point of the tissue stimulation lead(s) 20, The lead extension(s) 24, for example, may be tunneled from the implantation site of the IPG 18 up to the spinal column 62 using the tunneling tools 32.

Electrical stimulation is provided by the IPG 18 to the electrode array 22 in accordance with a set of stimulation parameters. Such stimulation parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 18 supplies constant current or constant voltage to the electrode array 22), pulse duration (measured in microseconds), and pulse frequency (measured in pulses per second, or Hertz). Electrical stimulation of the tissue will occur between two (or more) electrodes, one of which may be the case of the IPG 18, a patch electrode, or the like.

The IPG 18 may deliver stimulation energy to the electrode array 22 in any one or more different manners. For example, the IPG 18 may be capable of independently delivering constant current to the electrodes of the array 22 over multiple channels in either a multipolar or monopolar manner; delivering constant current to the electrodes of the array 22 over only a single channel in only a monopolar manner, or uniformly delivering constant voltage over multiple channels in either a multipolar or monopolar manner.

Significantly, the IPG 18 is capable of taking measurements that are indicative of the coupling efficiencies between the electrode array 22 and the surrounding tissue. Notably, in the case of SCS, the electrode array 22 fits snugly within the epidural space 66 of the spinal column 62, and because the tissue is conductive, there is an impedance associated therewith that indicates how easily current flows therethrough. Thus, the electrode impedance can be measured in order to determine the coupling efficiency between the respective electrode array 22 and the tissue. Other electrical parameter data, such as field potential and evoked action potential, may also be measured to ultimately determine the coupling efficiency between the electrodes 26 and the tissue.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference. For example, electrical data measurements can be made in response to alternating current (AC) or pulsatile electrical signals, which preferably use amplitudes and pulsewidths (e.g., 1 mA for 20 µs) that generate no physiological response for the patient (i.e., subthreshold), but can alternatively be performed in response to stimulation pulses.

The impedance measurement technique may be performed by measuring impedance vectors, which can be defined as impedance values measured between selected pairs of electrodes 22. The interelectrode impedance may be determined in various ways. For example, a known current (in the case where the IPG 18 is sourcing current) can be applied between a pair of electrodes 22, a voltage between the electrodes 22 can be measured, and an impedance between the electrodes 22 can be calculated as a ratio of the measured voltage to known current. Or a known voltage (in the case where the IPG is sourcing voltage) can be applied between a pair of electrodes 22, a current between the electrodes 22 can be measured, and an impedance between the electrodes 22 can be calculated as a ratio of the known voltage to measured current.

The field potential measurement technique may be performed by generating an electrical field at selected ones of the electrodes 22 and recording the electrical field at other selected ones of the lead electrodes 22. This may be accomplished in one of a variety of manners. For example, an electrical field may be generated conveying electrical energy to a selected one of the electrodes 22 and returning the electrical energy at the IPG case. Alternatively, multipolar configurations (e.g., bipolar or tripolar) may be created between the lead electrodes 22. Or, an electrode that is sutured (or otherwise permanently or temporarily attached (e.g., an adhesive or gel-based electrode) anywhere on the patient's body may be used in place of the case IPG outer case or lead electrodes 22. In either case, while a selected one of the electrodes 22 is activated to generate the electrical field, a selected one of the electrodes 22 (different from the activated electrode) is operated to record the voltage potential of the electrical field.

The evoked potential measurement technique may be performed by generating an electrical field at one of the electrodes 22, which is strong enough to depolarize the neurons adjacent the stimulating electrode beyond a threshold level, thereby inducing the firing of action potentials (APs) that propagate along the neural fibers. Such stimulation is preferably supra-threshold, but not uncomfortable. A suitable stimulation pulse for this purpose is, for example, 4 mA for 200 μS. While a selected one of the electrodes 22 is activated to generate the electrical field, a selected one or ones of the electrodes 22 (different from the activated electrode) is operated to record a measurable deviation in the voltage caused by the evoked potential due to the stimulation pulse at the stimulating electrode.

Further details discussing the measurement of electrical parameter data, such as electrode impedance, field potential, and evoked action potentials, as well as other parameter data, such as pressure, translucence, reflectance and pH (which can alternatively be used), to determine the coupling efficiency between an electrode and tissue are set forth in U.S. patent application Ser. No. 10/364,436, entitled "Neural Stimulation System Providing Auto Adjustment of Stimulus Output as a Function of Sensed Impedance," U.S. patent application Ser. No. 10/364,434, entitled "Neural Stimulation System Providing Auto Adjustment of Stimulus Output as a Function of Sensed Pressure Changes," U.S. Pat. No. 6,993,384, entitled "Apparatus and Method for Determining the Relative Position and Orientation of Tissue stimulation leads," and U.S. patent application Ser. No. 11/096,483, entitled "Apparatus and Methods for Detecting Migration of Tissue stimulation leads," which are expressly incorporated herein by reference.

Thus, it can be appreciated from the foregoing, that as each tissue stimulation lead 20 is introduced within the patient at different locations along a trajectory path, and in the case of SCS along the epidural space 66 of the patient 60, the IPG 18 can take measurements indicative coupling efficiencies between each of the electrodes 22 (and thus the tissue stimulation leads 20) and the tissue at the different locations. Although the measurement of parameters indicative of lead coupling efficiency have been described as being taken by the IPG 18, it should be appreciated that such measurements can be alternatively taken by any monitoring device capable of measuring and communicating coupling efficiency indicating parameters to an external control device.

Referring still to FIGS. 1 and 2, the external components 14 may include an external trial stimulator (ETS) 34, an external charger 36, a charging port 38, a hand-held programmers (HHP) 40, a clinicians programmer station (CPS) 42, percutaneous lead extension(s) 44 (if needed), and external cable(s) 46, and a tracking system 48.

The ETS 34 is capable of being used on a trial basis for a period of time (e.g., 7-14 days) after the tissue stimulation lead(s) 20 have been implanted, and prior to implantation of the IPG 18, to test the effectiveness of the stimulation that is to be provided. The tissue stimulation lead(s) 20 may be connected to the ETS 34 (via one or more connectors on the ETS 34) through the use of the lead extension(s) 44 and external cable(s) 46. The ETS 34 essentially operates in the same manner as the IPG 18 in that it can provide stimulation energy to the electrodes 22 and take measurements indicative of the coupling efficiency between the tissue stimulation leads 22 and the surrounding tissue.

When needed, an external charger 36 is non-invasively coupled with the IPG 18 through a communications link 50, e.g., an inductive link, allowing energy stored or otherwise made available to the charger 36 via the charging port 38 to be coupled into a rechargeable battery housed within the IPG 18. The HHP 40 may be used to control the IPG 18 via a suitable non-invasive communications link 52, e.g., an RF link. Such control allows the IPG 18 to be turned on or off, and generally allows stimulation parameters to be set within prescribed limits. The HHP 40 may also be linked with the ETS 34 through another communications link 54, e.g., an RF link, to likewise set stimulation parameters within prescribed limits. Thus, the HHP 40 is considered to be in "telecommunicative" contact with the IPG 18 or ETS 34.

The tracking system 48 is capable of tracking the location of the electrodes 22 on each tissue stimulation lead 20 relative to an anatomical structure, and in this case, the spinal column 62 of the patient 60 (shown in FIG. 4). The tracking system 48 may take the form of any conventional tracking system, such as a signaling system (e.g., a radio frequency (RF) triangulation or a multiple-dimension ultrasonic positioning system) or a conventional imaging system (e.g., a real-time computed tomography (CT) or fluoroscopic machine). In the case of a signaling tracking system, one or more transducers (which may be the electrodes 22 themselves) may be located on the tissue stimulation leads 20 and positioning signals can transmitted between these transducers and an external positioning system, such that the locations of the electrodes 22 and the anatomical reference can be determined in a three-dimensional coordinate system. If the signaling transducers are located on the tissue stimulation leads 20 a distance from the electrodes 22, the locations of the electrodes 22 can simply be determined from the known distances between the electrodes 22 and the known location of the transducer or transducers relative to one of the electrodes 22. In any event, as each tissue stimulation lead 20 is introduced within the patient at different locations along a trajectory path, and in the case of SCS along the epidural space 66 of the patient 60, the tracking system 48 can track the electrodes 22 of the tissue stimulation lead 20 at different locations relative to the spinal column 62 of the patient 60.

Modifying the stimulation parameters in the programmable memory of the IPG 14 after implantation (or in the ETS 34) may be performed by a physician or clinician using the CPS 42, which can directly communicate with the IPG 18 or indirectly communicate with the IPG 18 via the HHP 40. That is, the CPS 42 can be used by the physician or clinician to modify parameters of the stimulation pulses delivered by electrode array 22 near the spinal cord. In the illustrated embodiment, the CPS 42 is linked to the HHP 40 via another communications link 56, e.g., an infra red link. Alternatively, the CPS 42 can be coupled directly to the IPG 18 or ETS 34 via a communications link (not shown) or cable. Thus, the CPS 42 is considered to be in "telecommunicative" contact with the IPG 18 or ETS 34. The CPS 42 is also linked to the tracking system 48 via a communications link 58, e.g., a cable.

The overall appearance of the CPS 42 is that of a laptop personal computer (PC). Thus, in this embodiment illustrated in FIG. 4, the CPS 42 includes a user input device 68 (e.g., a keyboard, joystick, and a mouse) and a display (e.g., monitor, LED array, or the like) 70 housed in a case. The CPS 42 also comprises a processor (not shown) configured for performing the functions described below for the CPS 42, and input circuitry (not shown) configured for receiving information (e.g., measurements) from the IPG 18 over communications link 56 and for receiving information (e.g., tissue stimulation lead locations) from the tracking system 48 over communications link 57. The programming methodologies can be performed by executing software instructions in the processor contained within the CPS 42. Alternatively, such programming methodologies can be performed using firmware or hardware.

In any event, the CPS 42 may actively control the characteristics of the electrical stimulation generated by the IPG 18 (or ETS 34) to allow the optimum stimulation parameters to be determined based on patient feedback and for subsequently programming the IPG 18 (or ETS 34) with the optimum stimulation parameters.

Significantly, based on the measurements obtained from the IPG 18, the CPS 42 is configured for generating coupling efficiency information (i.e., information indicative of the coupling efficiency between the tissue stimulation lead 20 and tissue) for each of the locations at which the tissue stimulation lead 20 is placed, and based on the lead location information obtained from the tracking system 48, the CPS 42 is configured for generating lead location information (i.e., information indicative of the tracked location of the tissue stimulation lead relative to the spinal column 62 of the patient 60).

The coupling efficiency information may be derived from the measurements taken by the IPG 18 in any one or more of a variety of manners. For example, the coupling efficiency information for the tissue stimulation lead 20 may simply comprise the individual coupling efficiencies (e.g., impedance values, field potential values, etc.) between the respective electrodes 22 and the tissue. Of course, if the coupling efficiency between only one of the electrodes 22 and the tissue is available, then the coupling efficiency for the tissue stimulation lead 20 will comprise this single individual coupling efficiency for that electrode 22. Alternatively, the coupling efficiency information for the tissue stimulation lead 20 may be an average of the individual coupling efficiencies between the respective electrodes 22 and the tissue, the minimum of the individual coupling efficiencies between the respective electrodes 22, or the maximum of the individual coupling efficiencies between the respective electrodes 22. For each location of the tissue stimulation lead 20, the coupling efficiency information may comprise an absolute value or absolute values, or alternatively, the coupling efficiency information may comprise normalized or relative values for the locations of the tissue stimulation lead 20 that allow the user to compare them to get a sense of sufficient or insufficient coupling efficiencies. The displayed coupling efficiency information may be numerical or may take the form of a graph (e.g., a line graph or bar graph).

The tracking information may take any form that allows the user to gauge where the electrodes 22 are relative to the spinal column 62 of the patient 60. In the case where the tracking system 48 is a conventional imaging system, such as a fluoroscope or CT, the displayed tracking information may simply be the image of the electrodes 22 and surrounding structure of the spinal column. In the case where the tracking system 48 is, e.g., an RF triangulation or ultrasonic positioning system, the CPS 42 graphically generate representations of the electrodes 22 that may be superimposed over a pre-operative image of the spinal column 62 of the patient 60, or alternatively over an image of a spinal column 62 obtained from an atlas.

The CP 18 is configured for integrating the coupling efficiency information and tracking information together, so that they can be concurrently displaced together on the same screen. If the coupling efficiency information for the tissue stimulation lead 20 comprises a plurality of coupling efficiencies for the respective electrodes 22, the individual coupling efficiencies are preferably displayed adjacent to the respective electrodes 22, so that the user can easily associate each coupling efficiency with the respective electrode 22 with which it is associated. If the coupling efficiency information for the tissue stimulation lead 20 comprises a single coupling efficiency, then the single coupling efficiency may be displaced adjacent the determined location of the tissue stimulation lead 20. In an optional embodiment, the CPS 42 may concurrently display the coupling efficiency information for more than one location of the tissue stimulation lead 20, thereby providing a history of the coupling efficiency information in a single display screen.

With reference to FIGS. 5-8, methods of delivering a tissue stimulation lead 20 into the proper location in the epidural space 66 of the patient 60 will now be described. First, the tissue stimulation lead 20 is connected to the IPG 18 as it is outside the patient, the ETS 34, or any other monitoring device capable of measuring a parameter indicative of the coupling efficiency between the tissue stimulation lead 20 and the surrounding tissue.

As the clinician or physician advances the tissue stimulation lead 20 along a trajectory path in the epidural space 66, the tissue stimulation lead 20 is placed in different locations relative to the spinal column 62 of the patient 60, and in this case, location L1 (FIG. 5A), location L2 (FIG. 5B), and location L3 (FIG. 5C) as identified by the distal tip of the tissue stimulation lead 20. Of course, the locations are arbitrary, and can thus be identified by any portion of the tissue stimulation lead 20.

During the advancement of the tissue stimulation lead 20 within the epidural space 66, the IPG 18 is operated to measure parameters indicative of the coupling efficiency between the tissue stimulation lead 20 and the tissue when the tissue stimulation lead 20 is respectively at locations L1-L3. For example, the IPG 18 may convey electrical signals between tissue stimulation lead 20 and the tissue when the tissue stimulation lead 20 is respectively at locations L1-L3 (e.g., respectively from electrodes E1-E16) and measuring electrical parameters (e.g., an impedance or field potential) in response to the conveyance of the electrical signals. Of course, as discussed above, there are many other types of parameters (electrical and non-electrical) indicative of the coupling efficiency between the tissue stimulation lead 20 and tissue that can be measured. The measured parameters, in essence, are determined raw coupling efficiency data between the electrodes 22 and the tissue when the tissue stimulation lead 20 is at each of the different locations L1-L3.

During the advancement of the tissue stimulation lead 20 within the epidural space 66, the tracking system 48 is also operated to determine the location of the tissue stimulation lead 20 relative to an anatomical reference, and in this, case the spinal column 62 of the patient 60. As discussed above, the tracking system may acquire an image of the tissue stimulation lead 20 and anatomical reference or may determine the location of the tissue stimulation lead 20 at locations L1-L3 relative to the spinal column 62 of the patient 60 in a three-dimensional coordinate system.

The CPS 42 obtains the raw coupling efficiency data between the electrodes 22 and the tissue (i.e., the measured parameters) from the IPG 18, derives the coupling efficiency information from the raw coupling efficiency data, e.g., in any of the manners described above. The CPS 42 also obtains the locations of the tissue stimulation lead 20 relative to the spinal column 62 of the patient 60 from the tracking system 48, and in the case where the tracking system 48 is a three-dimensional positioning system, may involve graphically generating representations of the electrodes 22 and the spinal column 62 relative to each other. In the case where the tracking system 48 is a conventional imaging system, the CPS 42 may simply regenerate the imaging data of the tissue stimulation lead 20 and spinal column 62.

The CPS 42 then conveys the coupling efficiency information and the lead location information to the user, and in the preferred embodiment, displays this information to the user. In one embodiment, the CPS 42 displays the coupling efficiency information concurrently with the lead location information.

Figure 6A:
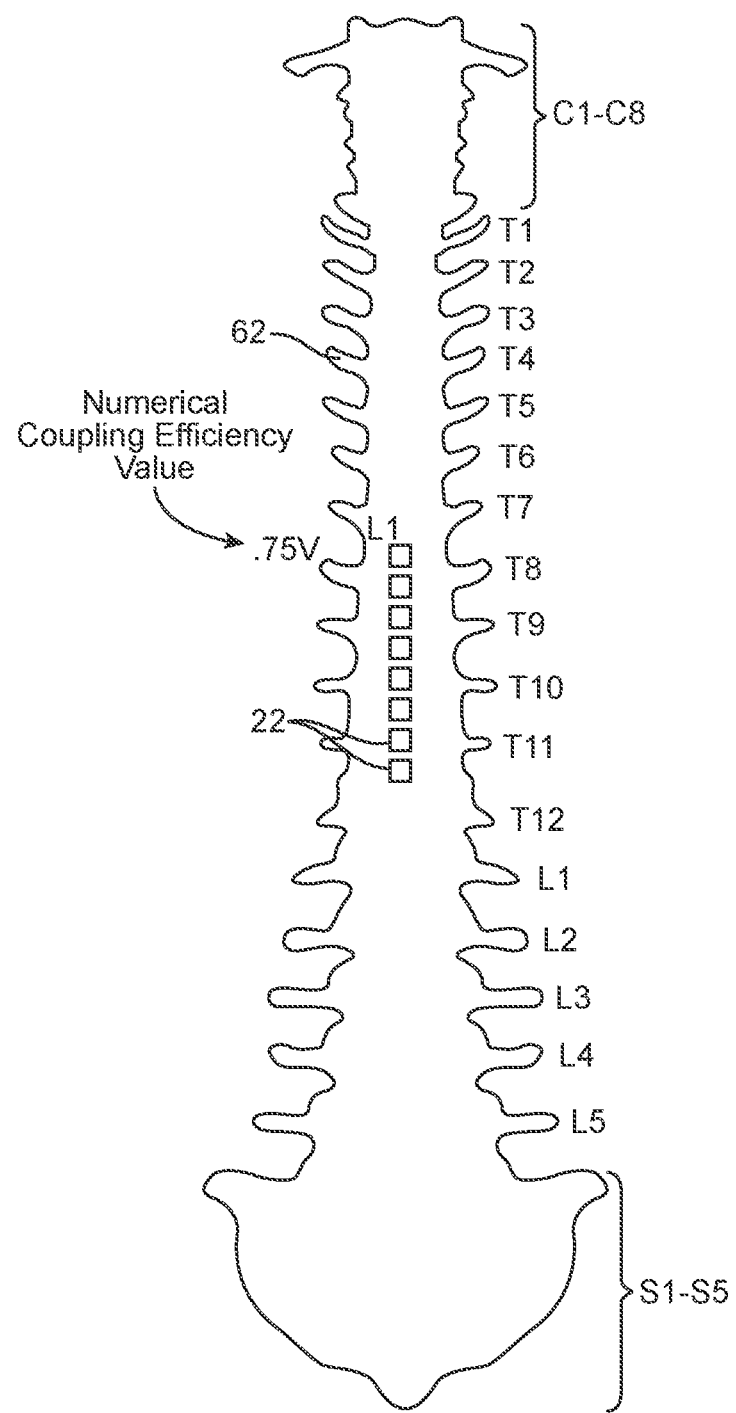
FIGS. 6A-6C are plan views of displays generated by a clinician programmer of the SCS system of FIG. 1, particularly showing lead coupling efficiency information in the form of numerical values.
Figure 6B:
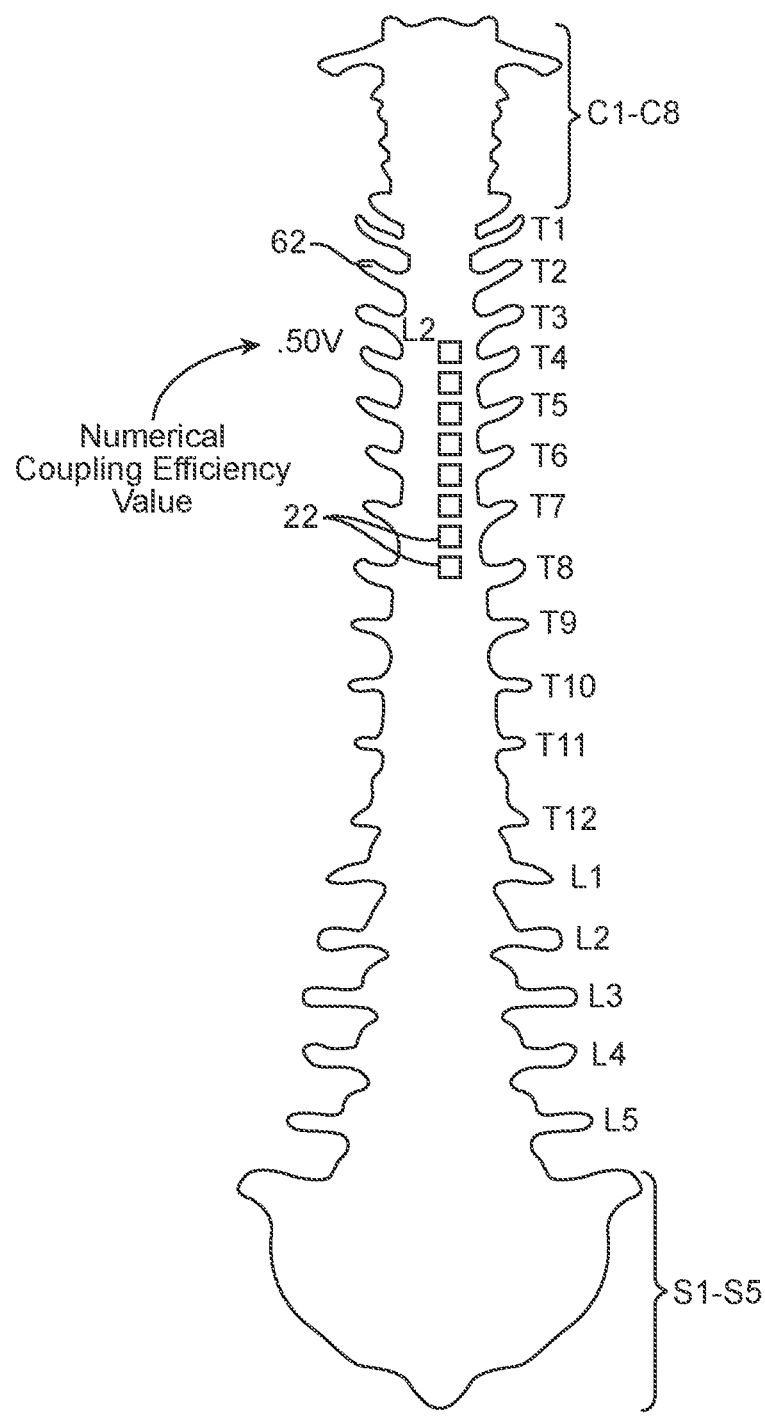
Figure 6C:
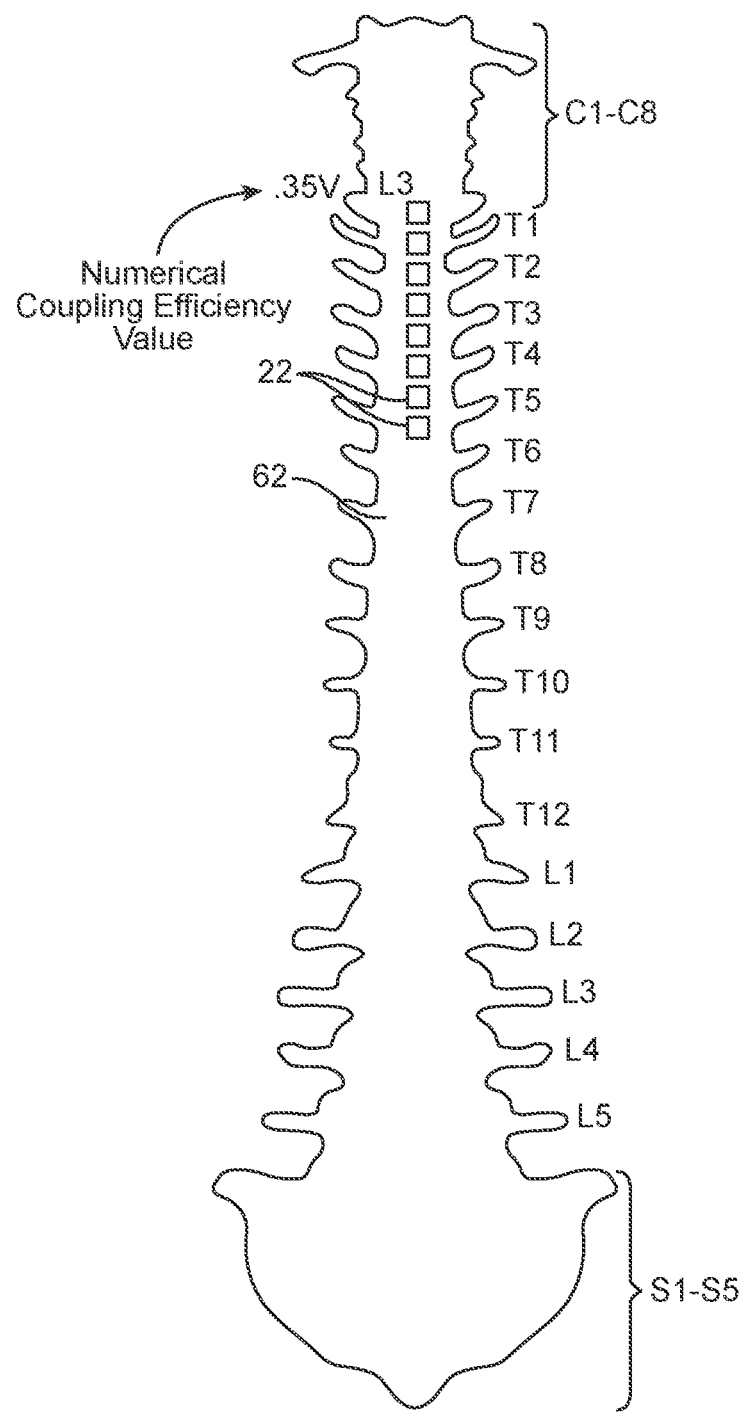
Figure 7A:
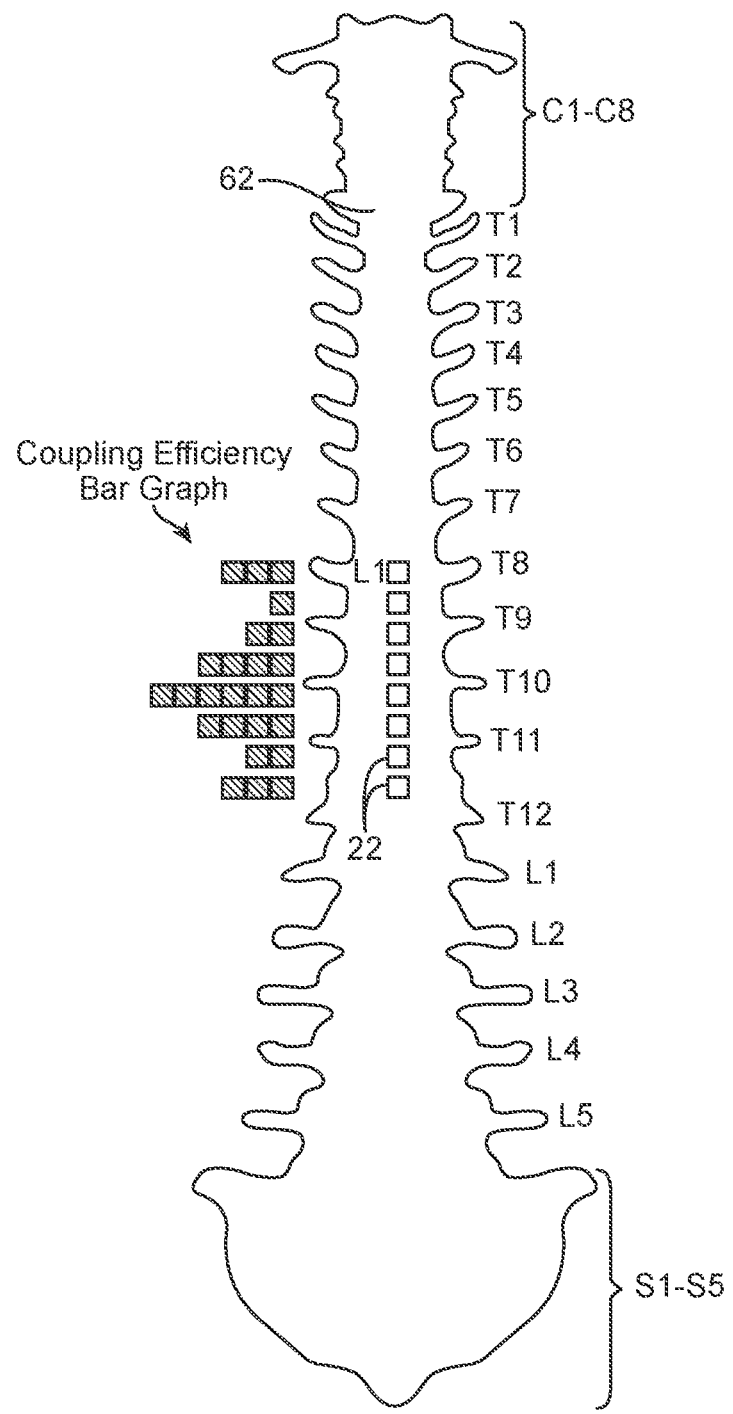
FIGS. 7A-7C are plan views of displays generated by a clinician programmer of the SCS system of FIG. 1, particularly showing lead coupling efficiency information in the form of a bar graph.
Figure 7B:
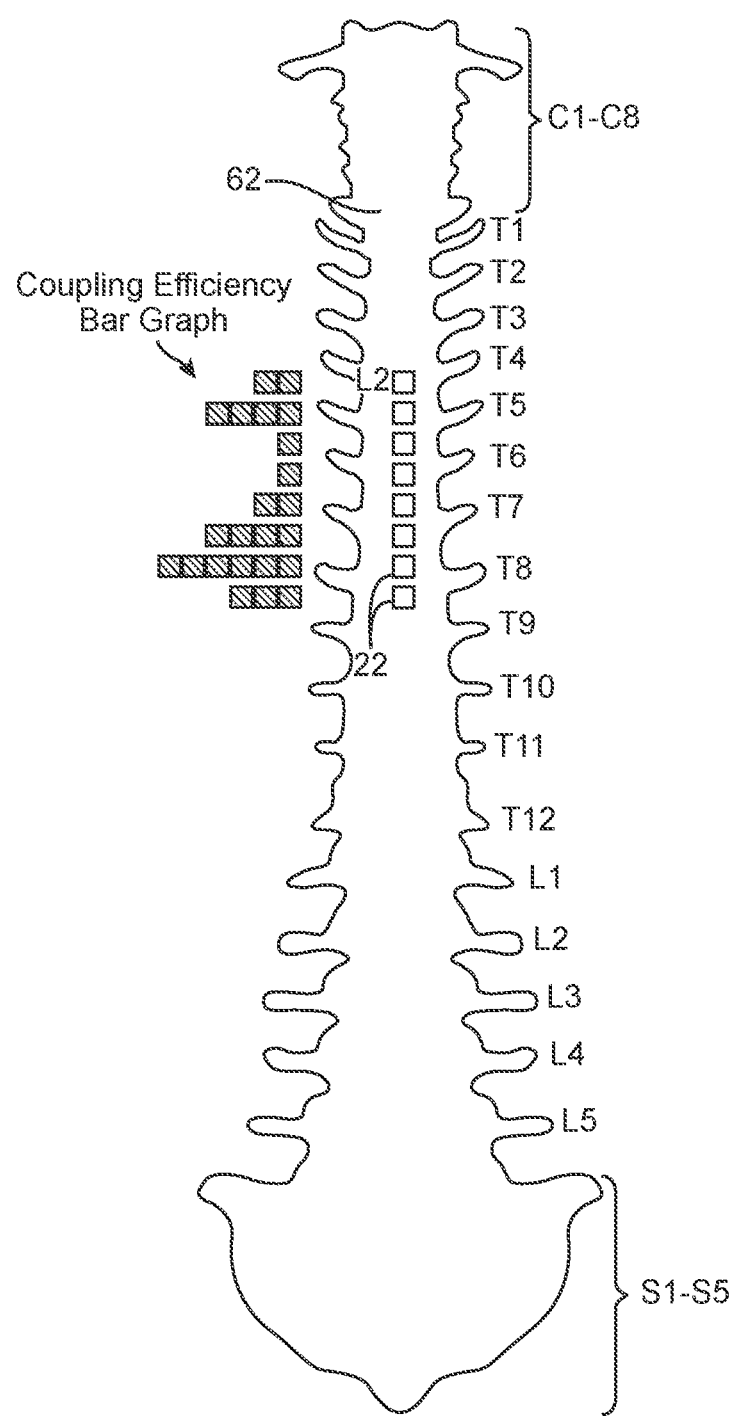
Figure 7C:
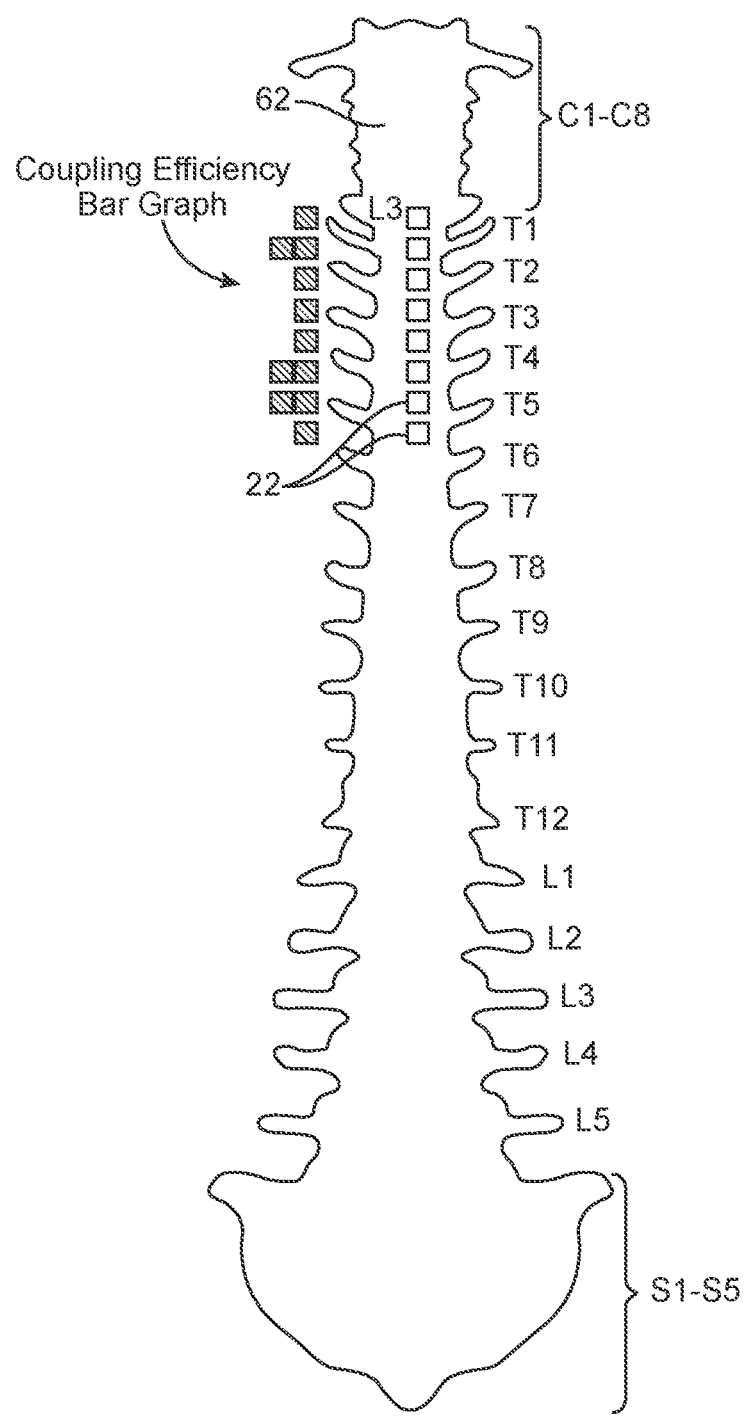
Figure 8:
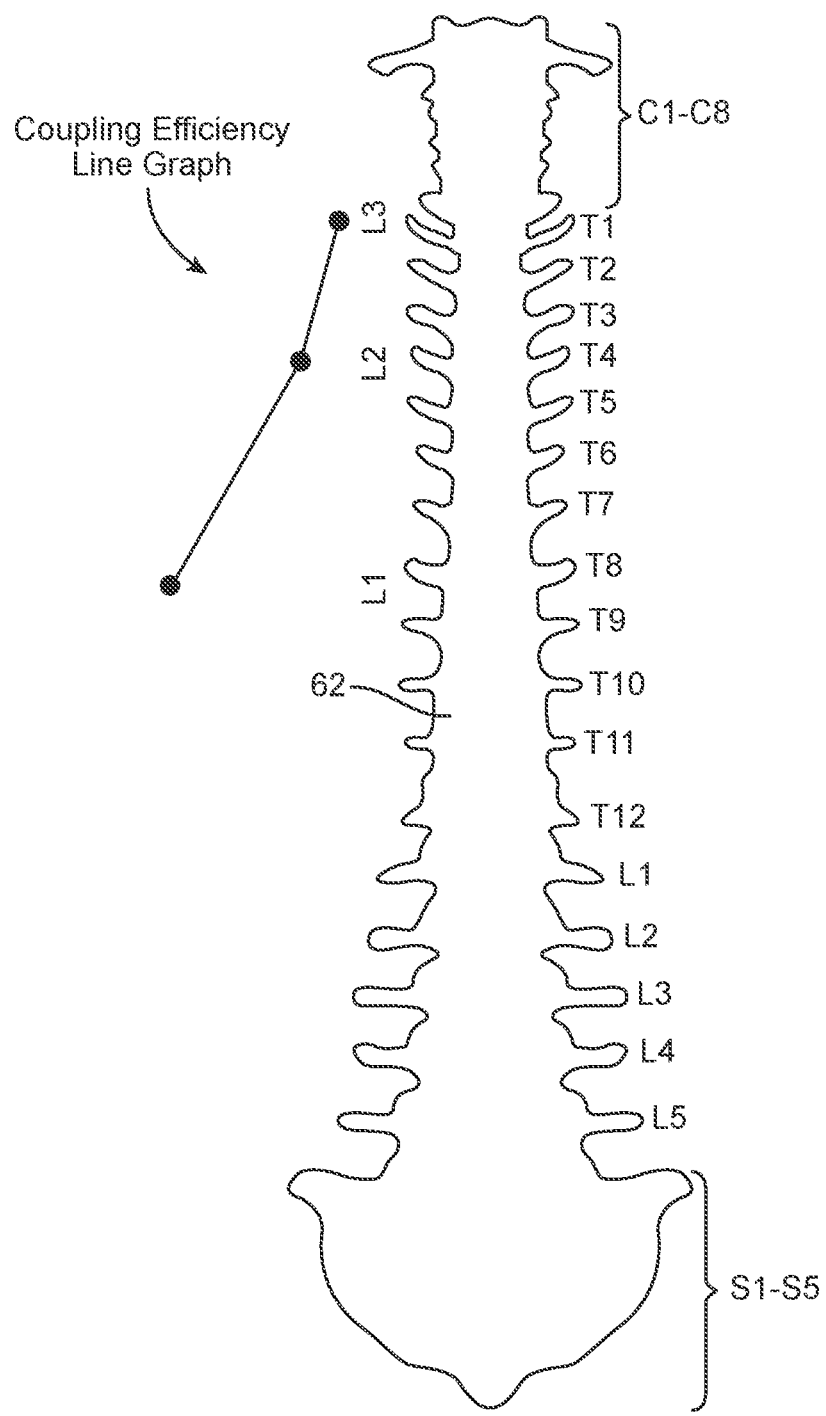
FIG. 8 is a plan view of a display generated by a clinician programmer of the SCS system of FIG. 1, particularly showing lead coupling efficiency information in the form of a line graph.

For example, as illustrated in FIGS. 6A-6C, the CPS 42 may display the electrodes 22 while the leads 20 are respectively at locations L1 (FIG. 6A), L2 (FIG. 6B), and L3 (FIG. 6C) and the corresponding coupling efficiencies of the tissue stimulation lead 20 at these respective locations. As there shown, the displayed coupling efficiencies take the form of a single field potential value displayed at the distal end of the tissue stimulation lead 20 for each location. Of course, as discussed above, the coupling efficiencies can take the form of any indicator of a coupling efficiency. For example, as illustrated in FIGS. 7A-7C, the coupling efficiencies may take the form of bar graphs that are respectively associated with the electrodes 22. As shown in FIG. 8, the CPS 42 concurrently displays the different locations of the tissue stimulation lead 20 relative to the spinal column 62. In this case, the CPS 42 displays the coupling efficiencies (each of which is associated with a different location) as a line graph along the spinal column 62.

With knowledge of the coupling efficiency of the tissue stimulation lead 20, the user will affix the tissue stimulation lead 20 at a suitable one of the locations L1-L3, preferably the location at which the coupling efficiency between the tissue stimulation lead 20 and the tissue is the highest. In an optional method, the user may operate the IPG 18 to convey stimulation energy to the electrodes 22 and into the spinal cord 66 as the tissue stimulation lead 20 is advanced within the epidural space 66 of the patient 60. As the tissue stimulation lead 20 is placed in different locations along the epidural space 66, the patient may sense paresthesia in different regions of the body. If the paresthesia is generally felt in the region requiring therapy, but is not effective, the user may determine the coupling efficiency from the display of the CPS 42, and if the coupling efficiency is low, the user may perform a corrective action. For example, the user reposition the tissue stimulation lead 20 within the epidural space 66 (e.g., a portion of the tissue stimulation lead 20 may be too far from the spinal cord 64 to provide efficiency stimulation thereto) or may adjust the stimulation parameters (e.g., increasing the amplitude of the stimulation energy).

Preferably, after tissue stimulation lead 20 is placed at each of the locations, the measurements and processing functions described herein are performed in real-time. That is, the time elapsed between the placement of the tissue stimulation lead 20 at each of the different locations L1-L3 along the trajectory path and the conveyance of the coupling efficiency information to the user at each respective location is less than one second.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system comprising a display; and
a controller connected to the display and configured to:
receive tracking data indicative of a tracked location of an implantable apparatus as the implantable apparatus is advanced through tissue, wherein the implantable apparatus includes an electrode;
receive coupling efficiency data between the electrode and the tissue as the implantable apparatus is advanced through the tissue; and
concurrently display coupling information indicative of the coupling efficiency data and tracking information indicative of the tracking data on the display,
wherein the tracking information is indicative of a tracked location of the implantable apparatus that includes an electrode relative to the tissue, and the coupling information is indicative of a coupling efficiency between the implantable apparatus and tissue at different locations as the implantable apparatus is advanced through the tissue.

2. The system of claim 1 wherein the tracking information is indicative of the different locations of the implantable apparatus relative to an anatomical structure of a patient.

3. The system of claim 1 wherein the controller is configured to display the coupling information as one or more numerical values.

4. The system of claim 1 wherein the coupling information is based on a measured electrical parameter.

5. The system of claim 4, wherein the measured electrical parameter is an impedance or a field potential.

6. The system of claim 1 wherein the controller is configured to display the coupling information as one or more graphs.

7. The system of claim 6 wherein the one or more graphs include a bar graph.

8. A system for locating an implantable apparatus that includes an electrode within a patient, comprising:
a tracker configured to track the location of the implantable apparatus relative to the tissue;
a monitor configured to take a measurement indicative of a coupling efficiency between the electrode of the implantable apparatus and tissue;
a display; and
a controller operably connected to the tracker, the monitor and the display being configured to generate coupling efficiency information based on the measurement from the monitor, generate tracking information based on the location, and concurrently display the coupling efficiency information and tracking information to a user.

9. The system of claim 8 wherein the implantable apparatus includes an implantable tissue stimulation lead, and the monitor is a neurostimulator further configured for delivering stimulation energy to the implantable tissue stimulation lead.

10. The system of claim 8, wherein the implantable apparatus includes an implantable tissue stimulation lead, and the controller is configured to display the coupling efficiency information as one or more numerical values.

11. The system of claim 8, wherein the implantable apparatus includes an implantable tissue stimulation lead, and the controller is configured to display the coupling efficiency information as one or more graphs.

12. The system of claim 8 wherein the implantable apparatus includes an implantable tissue stimulation lead, and the monitor device is configured to take the measurement by conveying an electrical signal between the tissue stimulation lead and the tissue, and measuring an electrical parameter in response to the conveyance of the electrical signal.

13. The system of claim 12, wherein the measured electrical parameter is an impedance or a field potential.

14. The system of claim 8, wherein the implantable apparatus includes an implantable tissue stimulation lead, and the tissue stimulation lead is configured to be introduced within the patient at different locations along a trajectory path, the monitor is configured to take measurements indicating the coupling efficiencies between the tissue stimulation lead and the tissue at the different locations, the lead tracker is configured to track the different locations of the tissue stimulation lead, and the controller is configured to generate the coupling efficiency information based on the measurements from the monitoring device, and to generate the tracking information based on the tissue stimulation lead locations.

15. The system of claim 14, wherein the displayed tracking information concurrently indicates the different locations of the tissue stimulation lead relative to the tissue.

16. The system of claim 14, wherein the tracking information is indicative of the different locations of the tissue stimulation lead relative to an anatomical structure of the patient.

17. A method, comprising:
generating tracking information, including tracking a location of an implantable apparatus that includes an electrode relative to tissue as the implantable apparatus is advanced through different locations within the patient;
generating coupling efficiency information, including determining a coupling efficiency between the implantable apparatus and the tissue at the different locations; and
concurrently displaying the tracking information and the coupling information.

18. The method of claim 17, further comprising conveying electrical signals between the implantable apparatus and tissue when the implantable apparatus is at the different locations, and measuring electrical parameters in response to the conveyance of the electrical signals, wherein the coupling efficiency information is generated based on the measured electrical parameters.

19. The method of claim 18, wherein each of the measured electrical parameters includes an impedance or a field potential.

20. The method of claim 18, wherein the displayed tracking information concurrently indicates the different locations of the implantable apparatus.

* * * * *